US012607606B2

(12) United States Patent
Yuan et al.

(10) Patent No.: US 12,607,606 B2
(45) Date of Patent: Apr. 21, 2026

(54) THERMAL SIMULATION EXPERIMENT METHOD FOR HYDROCARBON-WATER-ROCK INTERACTIONS BASED ON ISOTOPE TRACING

(71) Applicant: China University of Petroleum (East China), Qingdao (CN)

(72) Inventors: Guanghui Yuan, Qingdao (CN); Yingchang Cao, Qingdao (CN); Zihao Jin, Qingdao (CN); Keyu Liu, Qingdao (CN)

(73) Assignee: China University of Petroleum (East China), Qingdao (CN)

( * ) Notice: Subject to any disclaimer, the term of this patent is extended or adjusted under 35 U.S.C. 154(b) by 615 days.

(21) Appl. No.: 18/114,289

(22) Filed: Feb. 27, 2023

(65) Prior Publication Data

US 2023/0349864 A1 Nov. 2, 2023

(30) Foreign Application Priority Data

Apr. 27, 2022 (CN) ......................... 202210448976.X

(51) Int. Cl.
*G01N 30/06* (2006.01)
*G01N 24/08* (2006.01)
(Continued)

(52) U.S. Cl.
CPC ........... *G01N 30/06* (2013.01); *G01N 24/088* (2013.01); *G01N 30/7206* (2013.01);
(Continued)

(58) Field of Classification Search
CPC .. G01N 30/06; G01N 24/088; G01N 30/7206; G01N 33/24; G01N 2030/025;
(Continued)

(56) References Cited

U.S. PATENT DOCUMENTS

2003/0173072 A1 9/2003 Vinegar et al.
2003/0192693 A1 10/2003 Wellington et al.

FOREIGN PATENT DOCUMENTS

CN 103592380 A 2/2014
CN 104932033 A 9/2015
(Continued)

OTHER PUBLICATIONS

Geochimica et Cosmochimica Acta 248 (2019) (Year: 2019).*
(Continued)

*Primary Examiner* — Francis C Campanell
(74) *Attorney, Agent, or Firm* — Bayramoglu Law Offices LLC

(57) ABSTRACT

A thermal simulation experiment method for hydrocarbon-water-rock interactions based on isotope tracing is disclosed. N-eicosane, water and feldspar grains are first heated and reacted in a high temperature high pressure (HTHP) reactor. The reactor is quenched in water to room temperature and samples from the reaction are tested to obtain the composition and content of gas products, the isotopic compositions of gas products, the water solutions and authigenic clays, the nuclear magnetic resonance (NMR) spectra of the liquid hydrocarbons and water solutions, and textures and compositions of minerals. The genetic mechanisms of mass exchange and occurrence of hydrocarbon-water-rock interactions are analyzed. A thermal simulation experiment method using multiple isotope tracing, calibrates the exchange processes and paths for H and O between the hydrocarbons, water and minerals to provide evidence for deciphering the mechanism of the organic-inorganic interactions is disclosed.

12 Claims, 4 Drawing Sheets

(51) Int. Cl.
  *G01N 30/72*  (2006.01)
  *G01N 33/24*  (2006.01)
  *G01N 30/02*  (2006.01)

(52) U.S. Cl.
  CPC ....... *G01N 33/24* (2013.01); *G01N 2030/025* (2013.01); *G01N 2030/067* (2013.01)

(58) Field of Classification Search
  CPC .......... G01N 2030/067; G01N 24/081; G01N 33/241; G01N 30/02; G01N 30/72; Y02A 90/30
  USPC ........................................................ 585/18
  See application file for complete search history.

(56) References Cited

FOREIGN PATENT DOCUMENTS

| | | | |
|---|---|---|---|
| CN | 107305195 | A | 10/2017 |
| CN | 109828099 | A | 5/2019 |

OTHER PUBLICATIONS

Yuan Guanghui, et al., Genetic mechanism of dissolution of feldspars and carbonate minerals during diagenesis and its impact on reservoir poroperm, China University of Petroleum Doctoral Degree Dissertation, 2018, pp. 1-166.

Jie Wang, et al., Thermal Pyrolysis of Hydrocarbon Generation for Marine Hydrocarbon Sources in Marine Sequence of South China and Stable Carbon Isotopes of Gas Products, Natural Gas Geoscience, 2011, pp. 684-691, vol. 22 No. 4.

Guanghui Yuan, et al., Coupled mineral alteration and oil degradation in thermal oil-water-feldspar systems and implications for organic-inorganic interactions in hydrocarbon reservoirs, Geochimica et Cosmochimica Acta, 2019, pp. 61-87, vol. 248.

Xiuhong Wang, et al., Comparison of hydrocarbon generation characteristics of coal under the experimental conditions of water addition and no hydrothermal simulation, Fault-Block Oil&Gas Field, 2007, pp. 31-33, II-III, vol. 14 No. 4.

* cited by examiner

1

THERMAL SIMULATION EXPERIMENT METHOD FOR HYDROCARBON-WATER-ROCK INTERACTIONS BASED ON ISOTOPE TRACING

CROSS REFERENCE TO THE RELATED APPLICATIONS

This application is based upon and claims priority to Chinese Patent Application No. 202210448976.X, filed on Apr. 27, 2022, the entire contents of which are incorporated herein by reference.

TECHNICAL FIELD

The invention relates to the field of oil and gas geochemical experiment technology. A thermal simulation experiment method for hydrocarbon-water-rock interactions based on isotope tracing is disclosed.

BACKGROUND

In the burial process of petroliferous basin, organic-inorganic interactions in the source rocks and reservoirs are ubiquitous during the hydrocarbon forming and reservoir forming processes. The hydrocarbon-water-rock interactions at high temperature play an important role in the formation and preservation of deeply buried hydrocarbon reservoirs, and it is a hot issue in the present petroleum geology research. Thermal simulation experiment in high-temperature reactors is an important technology to study the processes and genetic mechanisms of geofluid-rock interactions. For the research of hydrocarbon-water-rock thermal simulation experiment at high-temperature, there still exist the following problem:

The occurrence of hydrocarbon-water-rock interactions at high-temperature is essentially a chemical process that involves mass exchange among different species. However, the present study of the interactions is usually based on the types, yields and morphology of the products formed in the thermal experiments. Because the samples used in the experiments have not been calibrated by isotope systematically, and controlled experiments have not been conducted, the products after reactions cannot be used to track the mass exchange between hydrocarbons, water, and minerals. Thus, it is unable to reveal the nature of organic-inorganic interactions from the perspective of chemical reaction process. Therefore, a simulation experiment method that can be used to reveal the genesis of hydrocarbon-water-rock interactions is of great importance.

SUMMARY

The purpose of this invention is to presents a thermal simulation experiment method for hydrocarbon-water-rock interactions based on isotope tracing. It can be used to resolve the existing problem.

In order to achieve the purpose of the invention, it provides the following technical solutions:

The invention provides a thermal simulation experiment method for hydrocarbon-water-rock interactions based on isotope tracing which involve the following steps:

Step 1: Conducting of hydrocarbon-water-rock thermal simulation experiments: put the n-eicosane, water and feldspar grains in reactors, and the reactors are sealed in the presence of argon. Heating the reactors for reaction and quench the reactor in water to room temperature as the experiments are finished.

Step 2: Testing of samples after reaction: the samples produced in the reactors in Step 1 west were tested, for the purpose of obtaining the composition and content of gas products, the isotopic compositions of gas products, the water solutions and authigenic clays, the High-field Nuclear Magnetic Resonance (NMR) spectra of the liquid hydrocarbons and water solutions, and the mineral textures and compositions.

Step 3: Decipher genesis of hydrocarbon-water-rock interactions: Based on the data obtained in Step 2, the genetic mechanisms of mass exchange and occurrence of hydrocarbon-water-rock interaction are analyzed.

In Step 1, the n-eicosane is $n-C_{20}H_{42}$ or $n-C_{20}D_{42}$; the water is $H_2{}^{18}O$, $D_2{}^{18}O$ or $D_2{}^{18}O$; the feldspar is K–feldspar.

Preferably, in the aforementioned thermal simulation experiment method for hydrocarbon-water-rock interactions based on isotope tracing, the mass ratio of n-eicosane, water and feldspar grains used in Step 1 is (0-10):(0-10):(0-1), and the mass of n-eicosane, water and feldspar cannot be zero at the same time.

Preferably, in the aforementioned thermal simulation experiment method for hydrocarbon-water-rock interactions based on isotope tracing, the reactors used in Step 1 need pretreatment. That is, all reactors were firstly heated at 740-760° C. for 7-9 hours, then, the reactors were cleaned with acetone and distilled water, and lastly were dried at 60° C.

Preferably, in the aforementioned thermal simulation experiment method for hydrocarbon-water-rock interactions based on isotope tracing, the temperature used in Step 1 is 339-341° C., and the reaction time is 9-11 days.

Preferably, in the aforementioned thermal simulation experiment method for hydrocarbon-water-rock interactions based on isotope tracing, the method for detecting the composition and content of the gas products in Step 2 is to place the reactors in the gas collection device and detect the composition and content of the gas product using the gas chromatography-mass spectrometry system.

Preferably, in the aforementioned thermal simulation experiment method for hydrocarbon-water-rock interactions based on isotope tracing, the method for detecting the gas product isotope in Step 2 is: after testing the composition and content of the gas product, use the gas chromatography isotope ratio mass spectrometer to detect the isotopic composition of the remaining gas product.

Preferably, in the aforementioned thermal simulation experiment method for hydrocarbon-water-rock interactions based on isotope tracing, the method for detecting the isotope of aqueous solution in Step 2 is as follows: separating the liquid products in the reactor to obtain the upper liquid hydrocarbon and the lower water solution; After evaporating the lower water solution at 75-85° C., purification was conducted using bromoethane filtration, activated carbon filtration, $C_{18}$ molecular sieve in sequence; and then use isotope ratio mass spectrometer to test the isotope of the water solution.

Preferably, in the aforementioned thermal simulation experiment method for hydrocarbon-water-rock interactions based on isotope tracing, the method for testing authigenic clay isotopes in Step 2 is to separate the liquid products in the reactor to obtain the upper liquid hydrocarbon and the lower water solution; Centrifuge the lower water solution and collect the precipitated clay; Separate the clay on the surface of feldspar grains in the reactor, mix the clay samples obtained from centrifuge and from feldspar surface, wash with dichloromethane and water in turn, and then use isotope ratio mass spectrometer to detect the isotope of authigenic clay.

Preferably, in the aforementioned thermal simulation experiment method for hydrocarbon-water-rock interactions based on isotope tracing, the method of High field NMR testing of liquid hydrocarbon and water solution in Step 2 is to separate the liquid products in the reactor to obtain the upper liquid hydrocarbon and lower water solution; Remove water from the upper liquid hydrocarbon using anhydrous copper sulfate to obtain liquid hydrocarbon; Mix the liquid hydrocarbon and the lower aqueous solution with the deuterium-free reagent respectively, and then use High-field NMR to test the NMR spectra of the liquid hydrocarbon and the lower aqueous solution respectively.

Preferably, in the aforementioned thermal simulation experiment method for hydrocarbon-water-rock interactions based on isotope tracing, the method for detecting the mineral textures and mineral composition in Step 2 is to dry the feldspar grains after reaction, then spray gold, and use scanning electron microscope (SEM) and Energy Dispersive Spectroscopy (EDS) to detect the mineral textures and mineral composition.

The above technical scheme shows that, comparing to the available techniques, the invention has the following beneficial effects:

The invention establishes a thermal simulation experiment method based on multiple isotope tracing, calibrates the exchange processes and paths of H and O between hydrocarbons, water and minerals, and provides direct evidence support for deciphering the mechanism of organic-inorganic interaction.

BRIEF DESCRIPTION OF THE DRAWINGS

In order to clearly explain the techniques and detailed examples of the present invention, the attached figures are briefly introduced.

FIG. 1A shows the D-NMR spectra of liquid hydrocarbons, FIG. 1B shows the D-NMR spectra of water solutions, FIG. 1C shows the H-NMR spectra of liquid hydrocarbons, and FIG. 1D shows the H-NMR spectra of water solutions.

FIG. 2A shows original feldspar surface, FIG. 2B shows feldspar surface in Experiment 2; FIG. 2C shows extensively leached feldspar (LF) in Experiment 3; FIG. 2D shows leached feldspar (LF) and euhedral boehmite (Bo) in Experiment 3; FIG. 2E shows extensively leached feldspar (LF) in Experiment 4; FIG. 2F shows leached feldspar (LF) and euhedral kaolinite in Experiment 4; FIG. 2G shows flower-like illite (muscovite) aggregates in Experiment 5; FIG. 2H shows lash-shaped boehmite in Experiment 5; FIG. 2I and FIG. 2J show thin plate-shaped illite (muscovite) aggregates on leached feldspar surface in Experiment 7; FIG. 2K shows subhedral plate-shaped illite (muscovite) on leached feldspar surface Experiment 8; FIG. 2L shows small euhedral illite (muscovite) on leached feldspar surface Experiment 9.

DETAILED DESCRIPTION OF THE EMBODIMENTS

Figure 1A:
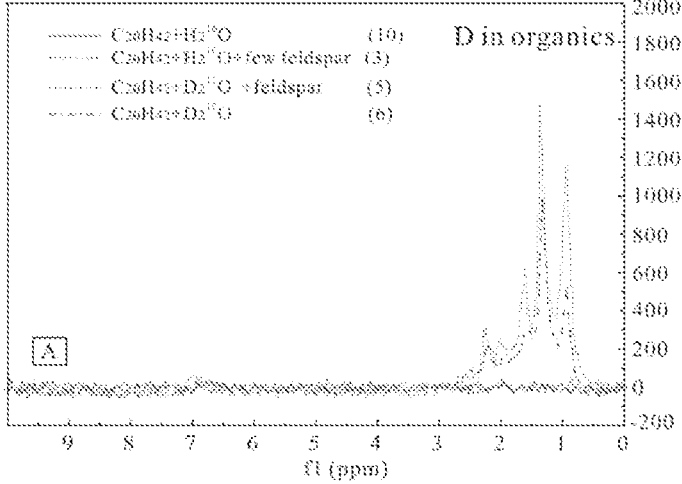
FIGS. 1A-1D show the high-field NMR spectra of liquid hydrocarbons and water solutions in Experiment 3, 4, 5, 6, 7 and 10.

The present invention provides a thermal simulation experiment method for hydrocarbon-water-rock interactions based on isotope tracing which involve the following steps:

Step 1: Conducting of hydrocarbon-water-rock thermal simulation experiments: put the n-eicosane, water and feldspar grains in reactors, and the reactors are sealed in the presence of argon. Heating the reactors for reaction and quench the reactor in water to room temperature as the experiments are finished.

Step 2: Testing of samples after reaction: the samples produced in the reactors in Step 1 were tested, for the purpose of obtaining the composition and content of gas products, the isotopic compositions of gas products, the water solutions and authigenic clays, the High-field Nuclear Magnetic Resonance (NMR) spectra of the liquid hydrocarbons and water solutions, and the mineral textures and compositions.

Step 3: Decipher genesis of hydrocarbon-water-rock interactions: Based on the data obtained in Step 2, the genetic mechanisms of mass exchange and occurrence of hydrocarbon-water-rock interaction are analyzed.

In Step 1, the n-eicosane is $n-C_{20}H_{42}$ or $n-C_{20}D_{42}$; the water is $H_2^{18}O$, $D_2^{18}O$ or $D_2^{18}O$; the feldspar is K–feldspar.

In the invention, the grain size of feldspar particles in Step 1 is preferably 150-250 $\mu m$. It is further preferably 170-230 $\mu m$, and more preferably 190 $\mu m$.

In the present invention, the feldspar grains used in Step 1 are preferably placed directly in the reactor with n-eicosane and water, or the feldspar grains are placed in the Hastelloy alloy mesh bag with a mesh size of 150, and then placed directly in the reactor with n-eicosane and water.

In the present invention, the mass ratio of n-eicosane, water and feldspar grains in Step 1 is preferably (0-10):(0-10):(0-1), and the mass of n-eicosane, water and feldspar grains is not zero at the same time. It is further preferably (3-9):(2-7):(0.5-1), more preferably 5:5:1.

In the invention, the reactor used in Step 1 is preferably a high temperature and high pressure Hastelloy reactor. The outer diameter of the reactor is preferably 20 mm, the wall thickness is preferably 5 mm, and the height is preferably 120 mm.

In the invention, the reactors used in Step 1 are pretreated before experiments. The pretreatment is preferably as follows: heat the reactor at 740-760° C. for 7-9 h, and then wash it with acetone, water and dry it successively after heating; It is further preferably heated at 744-756° C. for 7-8 h, more preferably heated at 750° C. for 8 h.

In the present invention, the reaction temperature in Step 1 is preferably 339-341° C., further preferably 340° C. The reaction time is preferably 9-11 days, further preferably 10 days.

In the present invention, the method for detecting the composition and content of the gas products in Step 2 is to place the reactors in the gas collection device and detect the composition and content of the gas product using the gas chromatography-mass spectrometry system.

In the present invention, the method for detecting the gas product isotope in Step 2 is: after testing the composition and content of the gas product, use the gas chromatography isotope ratio mass spectrometer to detect the remaining gas product isotope.

In the present invention, the method for detecting the isotope of aqueous solution in Step 2 is as follows: separating the liquid products in the reactor to obtain the upper liquid hydrocarbon and the lower water solution; After evaporating the lower water solution at 75-85° C., purification was conducted using bromoethane filtration, activated carbon filtration, Cis molecular sieve in sequence; and then use isotope ratio mass spectrometer to test the isotope of the water solution.

In the present invention, the method for testing authigenic clay isotopes in Step 2 is to separate the liquid products in the reactor to obtain the upper liquid hydrocarbon and the lower water solution; Centrifuge the lower water solution and collect the precipitated clay; Separate the clay on the surface of feldspar grains in the reactor, mix the clay samples obtained from centrifuge and from feldspar surface, wash with dichloromethane and water in turn, and then use isotope ratio mass spectrometer to detect the isotope of authigenic clay.

In the present invention, the method of High-field NMR testing of liquid hydrocarbon and water solution in Step 2 is to separate the liquid products in the reactor to obtain the upper liquid hydrocarbon and lower water solution; Remove water from the upper liquid hydrocarbon using anhydrous copper sulfate to obtain liquid hydrocarbon; Mix the liquid hydrocarbon and the lower aqueous solution with the deuterium-free reagent respectively, and then use High-field NMR to test the NMR spectra of the liquid hydrocarbon and the lower aqueous solution respectively.

In the present invention, the method for detecting the mineral textures and mineral composition in Step 2 is to dry the feldspar grains after reaction, then spray gold, and use scanning electron microscope (SEM) and Energy Dispersive Spectroscopy (EDS) to detect the mineral textures and mineral composition.

The technical solutions in the embodiments of the invention will be described clearly and completely below. Apparently, the described embodiments are only part of the embodiments of the invention, not all of them. Based on the embodiments in the invention, all other embodiments obtained by ordinary technicians in this field without creative work fall within the scope of protection of the invention.

The instant invention provides a thermal simulation experiment method for hydrocarbon-water-rock interactions based on isotope tracing which involve the following steps:

(1) Sample Preparation

Samples composed of n-$C_{20}H_{42}$, n-$C_{20}D_{42}$, $H_2^{16}O$, $D_2^{16}O$, $D_2^{18}O$ and K–feldspar (K$AlSi_3O_8$) grains were used in the embodiments. n-$C_{20}H_{42}$ was supplied by Aladdin Industrial Corporation (AIC, Shanghai) and has a purity greater than 99.5%; n-$C_{20}D_{42}$ was supplied by Canada C/D/N isotopes Inc., with 98.3% wt % deuterium; $H_2O$ used was ultrapure water from AIC, with δD of −31.3‰ and $δ^{18}O$ of −4.97‰. Pure $D_2^{16}O$ supplied by AIC was of 99.96 wt % deuterium. Pure $D_2^{18}O$ was supplied by the Wuhan Niuruide Special Gas Co., Ltd, with 99% deuterium and 97% $^{18}O$. K–feldspar grains with sizes between 150 μm to 250 μm were used in the experiments, and $δ^{18}O$ of the feldspar is 9.4‰-SMOW. K–feldspar grains were used directly or placed into Hastelloy alloy mesh bags (length 6 cm) with mesh size of 150 mesh.

(2) Thermal Experiments

The thermal experiments were conducted in HTHP Hastelloy pressure reactors (20 mm outside diameter, 5 mm wall thickness, and 120 mm height). All reactors were heated at 750° C. for 8 h to burn any organic matter. After heating, the reactors were cleaned with acetone and distilled water and were dried at 60° C.

Then n-eicosane (n-$C_{20}H_{42}$, n-$C_{20}D_{42}$), water ($H_2^{16}O$, $D_2^{16}O$, $D_2^{18}O$), feldspar grains or mesh bags with feldspar grains were placed into the Hastelloy pressure reactors, with different combinations of the species as listed in Table 1. Once loaded, the open ends of the reactors were purged with argon to remove air from the reactor; subsequently, the reactors were sealed in the presence of argon. Lastly, the reactors were weighed to obtain the weight before heating. Then, the reactors were placed in a single furnace and heated at 340° C. (error <±1° C.) for 10 days. After heating, the reactors were quenched to room temperature in cold water within 10 min. After drying, the reactors were weighed again to ensure no leakage during experiments.

TABLE 1

Summary of n-Eicosane (n-$C_{20}H_{42}$, n-$C_{20}D_{42}$)-water ($H_2O$, $D_2O$)-feldspars used in experiments.

| No. | n-$C_{20}H_{42}$ | n-$C_{20}D_{42}$ | $H_2^{16}O$ | $D_2^{16}O$ | $D_2^{18}O$ | K-feldspar |
|-----|-----|-----|-----|-----|-----|-----|
| 1 | 2 g | / | / | / | / | / |
| 2 | 2 g | / | / | / | / | 2 g |
| 3 | 2 g | / | 2 g | / | / | 20 mg in mesh bag |
| 4 | 2 g | / | / | 2 g | / | 20 mg in mesh bag |
| 5 | 2 g | / | / | / | 2 g | 2 g in mesh bag |
| 6 | 2 g | / | / | / | 2 g | |
| 7 | / | 2 g | 2 g | / | / | 2 g in mesh bag |
| 8 | 2 g | / | 2 g | / | / | 2 g in mesh bag |
| 9 | / | / | 2 g | / | / | 2 g |
| 10 | 2 g | / | 2 g | / | / | / |

(3) Analysis of Gases, Liquids, and Minerals after Experiments

Samples obtained in reactor were tested with the following processes:

Testing of gas composition and content. Place the reactors in the gas collection device and detect the composition and content of the gas product using the gas chromatography-mass spectrometry system. The data were listed in Table 2.

TABLE 2

| Gases | Experiments | | | | | | | | | |
|---|---|---|---|---|---|---|---|---|---|---|
| (mL/g) | 1 | 2 | 3 | 4 | 5 | 6 | 7 | 8 | 9 | 10 |
| $C_1$ | 0.078 | 0.088 | 0.531 | 0.557 | 5.742 | 1.460 | 0.323 | 0.117 | 0.000 | 0.280 |
| $C_2$ | 0.187 | 0.273 | 0.963 | 0.847 | 6.479 | 1.804 | 0.497 | 0.362 | 0.000 | 0.683 |
| $C_{2ene}$ | 0.002 | 0.003 | 0.004 | 0.003 | 0.031 | 0.013 | 0.006 | 0.004 | 0.000 | 0.003 |
| $C_3$ | 0.114 | 0.150 | 0.551 | 0.631 | 2.698 | 0.726 | 0.268 | 0.199 | 0.000 | 0.367 |
| $C_{3ene}$ | 0.017 | 0.027 | 0.031 | 0.025 | 0.153 | 0.061 | 0.029 | 0.036 | 0.000 | 0.031 |
| $iC_4$ | 0.000 | 0.000 | 0.001 | 0.002 | 0.020 | 0.001 | 0.000 | 0.000 | 0.000 | 0.003 |
| $nC_4$ | 0.034 | 0.038 | 0.141 | 0.072 | 0.563 | 0.176 | 0.072 | 0.051 | 0.000 | 0.107 |
| $iC_5$ | 0.002 | 0.002 | 0.003 | 0.000 | 0.008 | 0.002 | 0.003 | 0.003 | 0.000 | 0.003 |
| $nC_5$ | 0.002 | 0.003 | 0.001 | 0.002 | 0.006 | 0.003 | 0.004 | 0.004 | 0.000 | 0.002 |
| $H_2$ | 0.550 | 0.491 | 0.338 | 0.427 | 1.241 | 0.664 | 0.698 | 0.651 | 0.000 | 0.158 |
| $CO_2$ | 0.000 | 0.000 | 0.087 | 0.079 | 0.249 | 0.156 | 0.261 | 0.020 | 0.000 | 0.051 |

Gas yields of $C_1$-$C_5$, $H_2$ and $CO_2$ in different thermal experiments after 10-d heating.

Table 2 shows that gases were generated in all the experimental systems carried out with n-$C_{20}H_{42}$ (n-$C_{20}D_{42}$), and are dominated by $C_1$-n-$C_4$ alkanes and $H_2$. Isobutene (i-$C_4$), pentane (n-$C_5$, i-$C_5$), ethene and propene were also generated, but with comparatively lower yields. $H_2$ was generated in both the anhydrous and hydrous systems. However, $CO_2$ was detected only in the hydrous systems. Overall, the yields of hydrocarbon gases were highest in the Experiments 5 and 6 with the presence of $D_2{}^{18}O$ water, followed by Experiment 4 with $D_2{}^{16}O$ water, and lastly Experiment 7 with n-$C_{20}D_{42}$ (Table 2). All isotopically labeled systems generated more hydrocarbon gases and $H_2$ than those experiments without labeled reactants. In addition, the presence of feldspar was accompanied with high yields of hydrocarbon gases, $H_2$ and $CO_2$ in Experiment 3 (compared with Experiment 10) and Experiment 5 (compared with Experiment 6) (FIG. 1), regardless of with or without $^{18}O$ labeled water.

b. Testing of isotopic composition of $CH_4$, $C_2H_6$ and $CO_2$ gases. After the GC analysis, the remaining gas components were used for isotope analysis using a Thermo Fisher MAT-253 GC-isotope ratio mass spectrometry (GC-IRMS). This analysis was performed on a VG Isochrom II interfaced to an HP 5890 GC fitted with a Poraplot Q column (30 mm×0.32 mmi·d·). The isotopic composition of $CH_4$ and $C_2H_6$ generated in the Experiments 3 and 4 were determined and presented in Table 3.

TABLE 3

Isotopic composition of $CH_4$ and $C_2H_6$ generated in thermal systems with and without δD labeled water.

| No. | Species combination | $\delta^{13}C$ (‰) | | $\delta D$ (‰) | | AT D/H | |
|---|---|---|---|---|---|---|---|
| | | $CH_4$ | $C_2H_6$ | $CH_4$ | $C_2H_6$ | $CH_4$ | $C_2H_6$ |
| 3 | n-$C_{20}H_{42}$ + $H_2{}^{16}O$ + 20 mg K-feldspar | −58.490 | −41.23 | −287 | −313 | 0.0111 | 0.0107 |
| 4 | n-$C_{20}H_{42}$ + $D_2{}^{16}O$ + 20 mg K-feldspar | −58.342 | −41.42 | 938607 | 185123 | 12.7661 | 2.8172 |

The data in Table 3 show that the $\delta^{13}C$ compositions of $CH_4$ and $C_2H_6$ in the hydrous systems with and without δD labeled water are almost identical. In contrast, the δD composition of the $CH_4$ and $C_2H_6$ in the different hydrous systems varies significantly. In the n-$C_{20}H_{42}$+$H_2{}^{16}O$+20 mg feldspar system (Experiment 3), the δD (AT % D/H) values of $CH_4$ and $C_2H_6$ are −287‰ (0.0111) and −313‰ (0.0107), respectively. While in Experiment 4 (n-$C_{20}H_{42}$+$D_2{}^{16}O$+20 mg feldspar), the δD (AT % D/H) values of $CH_4$ and $C_2H_6$ are 938607‰ (12.7661) and 185123‰ (2.8172), respectively, higher than that in Experiment 3.

The isotopic composition of $CO_2$ generated in experiments 3-6 was determined and present in Table 4.

TABLE 4

Isotopic compositions of $CO_2$ in systems with and without $\delta^{18}O$ labeled water.

| No. | Species combination | $\delta^{13}C$ (‰) | $\delta^{18}O$ (‰) | At $^{18}O/^{16}O$ |
|---|---|---|---|---|
| 3 | n-$C_{20}H_{42}$ + $H_2{}^{16}O$ + 20 mg K-feldspar | −15.17 | −16.78 | 0.1967 |
| 4 | n-$C_{20}H_{42}$ + $D_2{}^{16}O$ + 20 mg K-feldspar | −14.97 | −16.77 | 0.1967 |
| 5 | n-$C_{20}H_{42}$ + $D_2{}^{18}O$ + 2 g K-feldspar | −246 | 60631 | 11.00 |
| 6 | n-$C_{20}H_{42}$ + $D_2{}^{18}O$ | −250 | 95731 | 16.25 |

Table 4 show that the $\delta^{18}O$ values of the $CO_2$ in Experiments 3 and 4 without $\delta^{18}O$ labeled water are close to −16.77‰, with an AT % $^{18}O/^{16}O$ (atom ratio between $^{18}O$ and $^{16}O$) value of 0.1967, while in Experiments 5 and 6 with $\delta^{18}O$ labeled water, the $\delta^{18}O$ values are much higher. In Experiment 6 (n-$C_{20}H_{42}$+$D_2{}^{18}O$), the $\delta^{18}O$ value of the $CO_2$ reaches up to 95731‰, with an At % $^{18}O/^{16}O$ value of 16.25; in Experiment 5 (n-$C_{20}H_{42}$+$D_2{}^{18}O$+feldspar), the $\delta^{18}O$ value of the $CO_2$ is 60631‰, with an At % $^{18}O/^{16}O$ value of 11.00, which is lower than in Experiment 6 without K−feldspar. In addition to the large differences of the $\delta^{18}O$ values, the $\delta^{13}C$ values of $CO_2$ also show big differences between the experiments with and without $\delta^{18}O$ labeled water, with $\delta^{13}C$ values of approximately −15‰ in Experiments 3 and 6, and approximately −250‰ in Experiments 5 and -6, respectively (Table 4).

c. Testing of isotopic composition of water. After thermal experiments, the liquid organics-water solutions were firstly separated to obtain the liquid hydrocarbons at the upper and the water solutions at the lower part of the reactors. Each water sample was then filtered with bromoethane and activated carbon after low-temperature evaporation (80° C.) to remove the organic solutes (e.g., alcohols, organic acids, etc.). Finally, the water samples were purified using $C_{18}$ molecular sieves. The treated water samples were then analyzed using the LabRAM HR800 Raman spectrometer with a 532 nm laser excitation. Here no dissolved organic molecules were detected in the water samples. After purification, the water samples were analyzed using the Thermo Fisher MAT-253 IRMS to obtain the hydrogen and oxygen isotope composition. The D/H ratios were reported using both the direct atomic abundance ratios (At D/H) and the delta values ($\delta D$) in unit of ‰ relative to $V_{SMOW}$, and the $^{18}O/^{16}O$ were reported using the delta values ($\delta^{18}O$) in unit of ‰ relative to $V_{SMOW}$. The isotopic composition of the original water and water after heating was determined for Experiments 7-10 were listed in Table 5.

TABLE 5

Isotopic compositions of water and clay minerals
in systems with and without $\delta D$ labeled n-eicosane

| No. | Water after experiments | | | Clays after experiments | |
| --- | --- | --- | --- | --- | --- |
| | $\delta D$ (‰) | AT D/H | $\delta^{18}O$ (‰) | $\delta D$ (‰) | AT D/H |
| Initial water | −31.3 | 0.01508 | −4.97 | / | / |
| 7 | 36997 | 0.5883 | −1.17 | 12943.22 | 0.219 |
| 8 | −38.3 | 0.014953 | 0.23 | 162.39 | 0.018 |
| 9 | −36.9 | 0.014968 | −4.73 | 22.33 | 0.016 |
| 10 | −37.3 | 0.014962 | −4.08 | / | / |

Table 5 show that with the presence of n-$C_{20}D_{42}$ in Experiment 7, the water after experiment exhibited a much higher $\delta D$ (AT % D/H) value of 35935‰ (0.5883). Without addition of n-$C_{20}D_{42}$, the $\delta D$ isotope composition of water after heating was much lower, with $\delta D$ (AT % D/H) values of around −37‰ (0.014969) (Table 5). The original water has a $\delta^{18}O$ value of −4.97‰ with the presence of K−feldspar, the $\delta^{18}O$ value of water after heating with K−feldspar became higher, ranging from −4.73‰ to 0.23‰ d. Testing of isotopic composition of clays. Newly formed clay minerals precipitated in the water solution were collected by centrifuging of the waters. Feldspar grains were cleaned using dichloromethane and distilled water to remove the oil covering the mineral surfaces. Clays precipitated on feldspar grain surfaces were then separated gently by milling using pestle and mortar, and peeling fine debris from feldspar grains was then mixed with distilled water and stirred with a glass rod to collect the suspension on the upper layer. The suspension fluid was centrifuged at 2,000 rpm to collect the precipitated clay minerals. Clays obtained from water and feldspar surfaces were then repeatedly cleaned using dichloromethane and distilled water times to remove possible residual organic matter. Clay samples were identified using SEM, EDS and Raman spectrometer to ensure no residual of organics. Lastly, the clays were dried and dispersed for isotope analysis. Prepared clays were analyzed using the Thermo Fisher MAT-253 IRMS to obtain the hydrogen isotope composition. $\delta D$ composition of newly generated clay minerals in Experiments 7-9 was determined (Table 5).

Table 5 shows that the clay minerals in Experiments 8 and 9 without n-$C_{20}D_{42}$ have $\delta D$ (AT % D/H) values of 162.39‰ (0.00018) and 22.33‰ (0.00016), respectively. In Experiment 7 with $C_{20}D_{42}$, the $\delta D$ (AT % D/H) value of the authigenic clay is 12943.22‰ (0.00219), and thus much higher than in Experiments 8 and 9 without n-$C_{20}D_{42}$.

e. Testing of High-field NMR spectra of liquid alkanes and waters. Separate the liquid products in the reactor to obtain the upper liquid hydrocarbon and the lower water solution. After separation and centrifuge, anhydrous copper sulfate (ACS) was added in the separated liquid organics to remove residual water, this process was repeated until no color change of the ACS was visible. Separated liquid alkane and water samples were mixed with deuterium free reagents to homogenize the field. The samples were then examined using the AVANCE III 600 MHz Nuclear Magnetic Resonance (NMR) with a broadband BBFO probe to gather the $^1H$ NMR spectrum and $^2H$ NMR spectrum of each sample. The standard ZG30 echo pulse sequence was used for the $^1H$ NMR spectrum and the standard ZG echo pulse sequence for the $^2H$ NMR spectrum. The pulse lengths were kept as short as possible to minimize any artefacts in the spectra due to finite pulse length effects. For the $^1H$ NMR spectrum, the 90° pulse lengths were 10.5 μs and the echo delay was 40 μs. For the $^2H$ NMR spectrum, the 90° pulses were 149 μs and the delay between pulses was 40 μs. In all experiments, the final delay prior to acquisition was set such that a few data points were collected before the top of the echo. This allows us to manually correct the phase of the FID and shift the points in the time domain before removing the points before the top of the echo. This process is important for obtaining spectra with a flat baseline. At the beginning of each series, the sample set point temperature was raised to 25° C. and the sample was allowed to equilibrate for at least 20 minutes. Spectra were then collected four times for the $^1H$ NMR spectrum and 32 times for the $^2H$ NMR spectrum. At the end of each series, the temperature was set to starting conditions of the experiment series and the spectrum was collected again to verify sample stability. The results were presented in FIGS. 1A-1D.

Figure 1B:
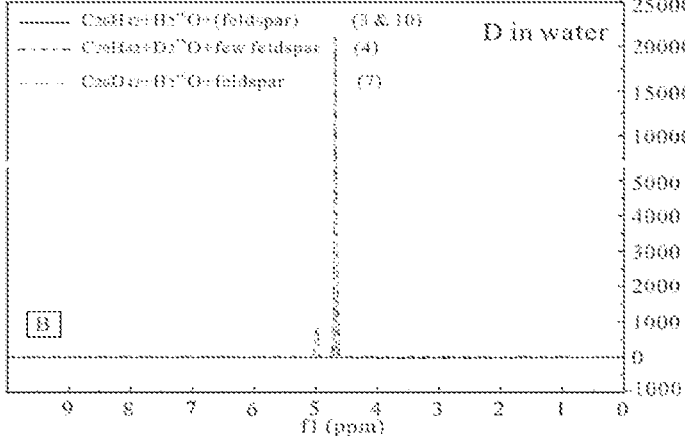
Figure 1C:
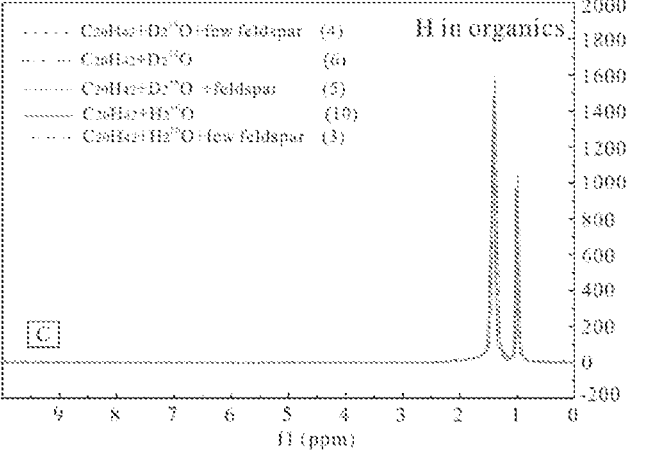
Figure 1D:
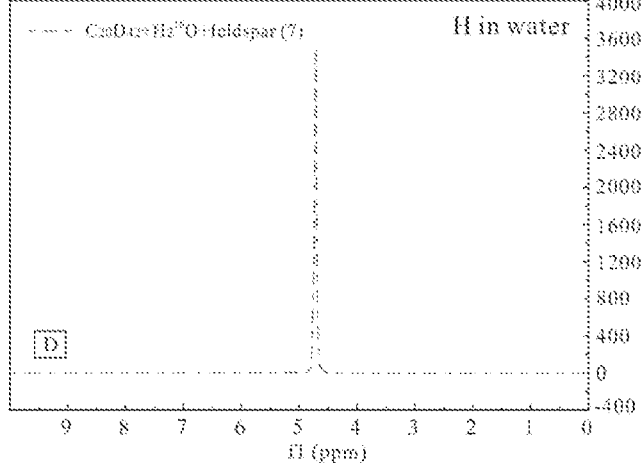
Figure 2A:
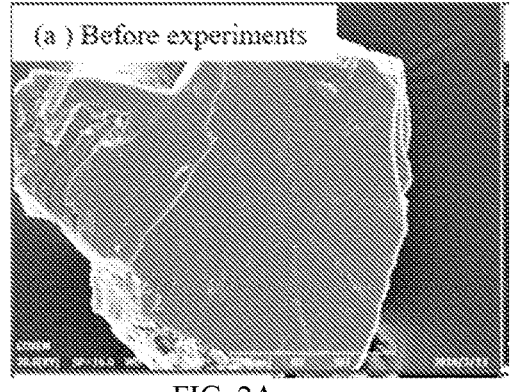
FIGS. 2A-2L show the SEM images of original K–feldspar, leached K–feldspar and authigenic minerals after experiments.
Figure 2B:
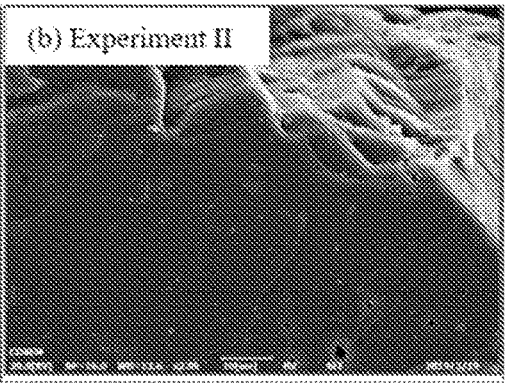
Figure 2C:
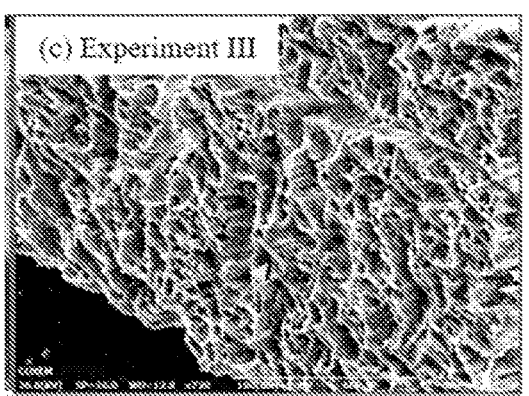
Figure 2D:
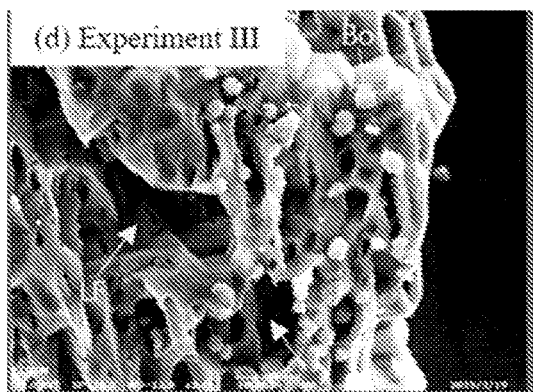
Figure 2E:
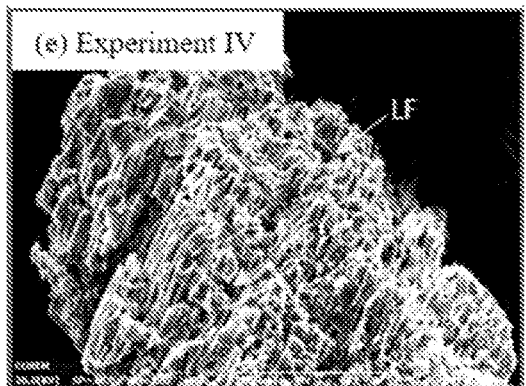
Figure 2F:
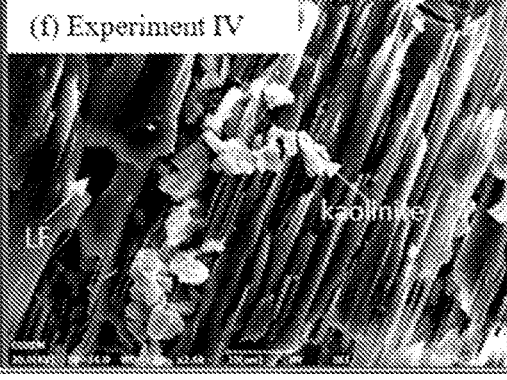
Figure 2G:
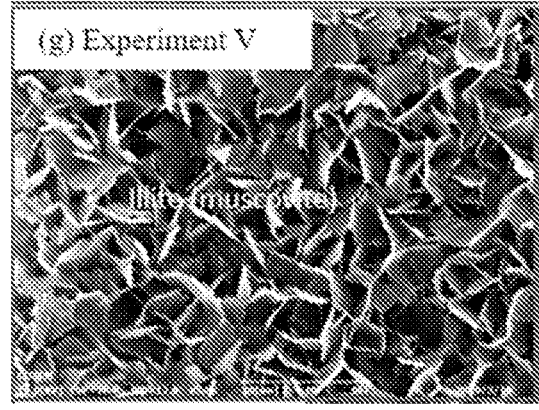
Figure 2H:
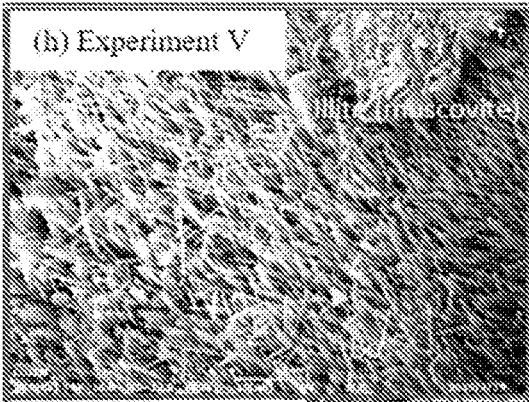
Figure 2I:
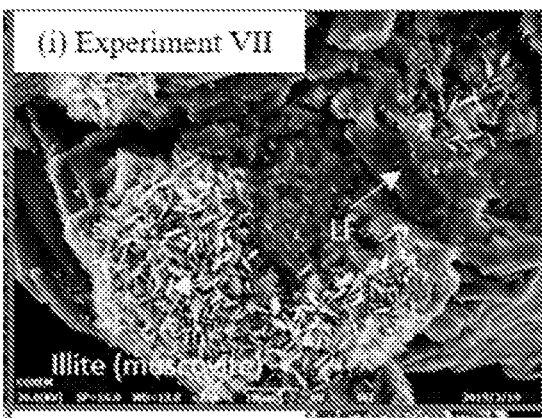
Figure 2J:
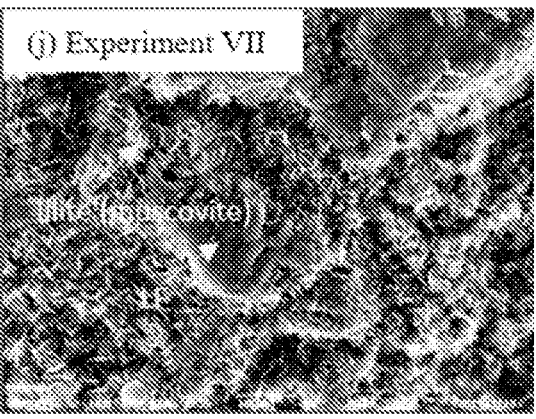
Figure 2K:
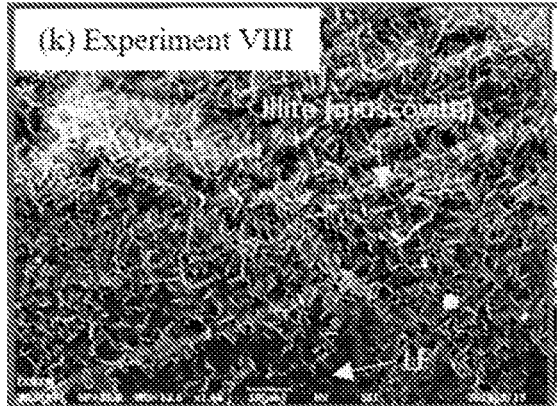
Figure 2L:
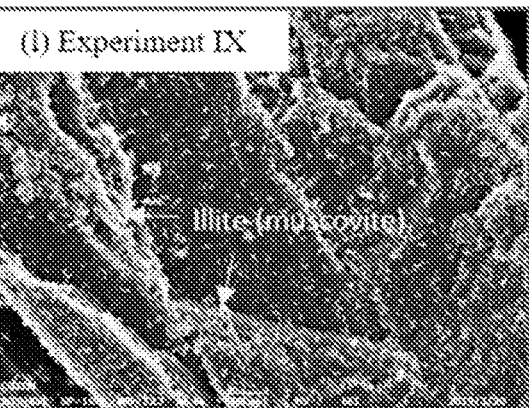

FIGS. 1A-1D show that after heating, neither water nor liquid organics in Experiments 3 (n-$C_{20}H_{42}$+$H_2^{16}O$+20 mg feldspar) and 10 (n-$C_{20}H_{42}$+$H_2^{16}O$) contained detectable deuterium (FIGS. 1A and 1B). In contrast, the resulting liquid organics in Experiments 5 (n-$C_{20}H_{42}$+$D_2^{18}O$+2 g feldspar) and 6 (n-$C_{20}H_{42}$+$D_2^{18}O$) with $\delta D$ labeled water contained detectable amounts of deuterium (FIG. 1A). In Experiment 7 with a combination of n-$C_{20}D_{42}$, $H_2O$ and K−feldspar, the resulting water contained a detectable amount of deuterium (FIG. 1B), consistent with the tested isotopic composition (Table 5). After heating, the liquid organics in the systems with n-$C_{20}H_{42}$ and the water in the systems with $H_2O$ still show strong hydrogen signal (FIGS. 1C and 1D).

f. Testing of mineral textures and compositions. After the experiments, the feldspars grains were firstly cleaned using acetone and distilled water to remove the oil covering the mineral surfaces. The cleaned mineral grains were then fixed on aluminum stubs with conducting tape and coated with gold. The minerals were then identified using the Coxem-30 plus SEM to describe the textures of the K−feldspar and secondary minerals. A Bruker energy dispersive spectrometer (EDS) system (XFlasher Detector 430-M). SEM images were presented in FIGS. 2A-2L.

The SEM images of feldspars before and after thermal experiments show that feldspars in the anhydrous $n-C_{20}H_{42}+$ feldspar system experienced no dissolution (FIGS. 2A-2B), and no secondary minerals were generated after 10 days. In the hydrous systems, distinct feldspar dissolution occurred, with precipitation of secondary minerals (FIGS. 2C-2L). For the systems with only 20 mg feldspars, these feldspars were leached quite extensively (FIGS. 2C-2F), and secondary minerals including kaolinite and illite were observed to be present on K–feldspar surfaces and in the water solutions. For the systems with 2 g feldspars, the grains were dissolved, and illite and muscovite were commonly observed on K–feldspar surfaces, and also in the water solutions (FIGS. 2G-2L). In the system with only $H_2O$ and feldspar, feldspar was also altered with the precipitation of illite.

(4) Genetic Mechanisms of Hydrocarbon-Water-Rock Interactions

With the results obtained in the last step, the genetic mechanism of hydrocarbon-water-rock interactions was analyzed.

In a hot anhydrous $n-C_{20}H_{42}$–feldspar system, feldspar is not altered following $n-C_{20}H_{42}$ degradation, indicating no organic-inorganic interactions in the absence of water. In the hot hydrous $n-C_{20}H(D)_{42}$-$H(D)_2O$–feldspar systems, distinct mass exchange occurs among the organic and inorganic components, leading to extensive organic-inorganic interactions. Here, the results demonstrate that in the generic $n-C_{20}H(D)_{42}$-$H(D)_2O$–feldspar systems, both $n-C_{20}H_{42}$ and water provided hydrogen for the generated gaseous and liquid hydrocarbons; besides water, $n-C_{20}H_{42}$ also provided hydrogen for authigenic OH-containing clays. After heating, an significant enrichment of deuterium (δD) was identified in the liquid hydrocarbons in the $n-C_{20}H_{42}$-$D_2O$–(feldspar) systems and in the water of the $n-C_{20}D_{42}$-$H_2O$–(feldspar) systems, indicating an extensive formation and recombination of free radicals (e.g., D*, H*, OD*, OH*, $R_H$*, $R_D$*) at elevated temperature. These promote the mass exchange between organic compounds and water. Apart from water, K–feldspar ($KAlSi_3O_8$) also provides oxygen for generated $CO_2$, as verified by the difference of $\delta^{18}O$ composition of $CO_2$ in the systems with and without feldspar. The dilution of $\delta^{18}O$ in $D_2^{18}O$ water after reaction in an $n-C_{20}H_{42}$-$D_2^{18}O$–feldspar system indicated that oxygen from feldspar was initially transferred to water via mineral dissolution, and subsequently invoked in $CO_2$ generation.

The δD and $\delta^{18}O$ data, and HF-NMR H/D spectra of newly formed species in the hydrous systems demonstrate that water serves as a bridge (solvent and also a reactant) for mass exchanges among the organic and inorganic fractions, probably via formation (initiation) and consumption (termination) of free radicals and ions. Hence, the presence of water highlights its function to erase boundaries and to enable reactions among organic and inorganic components at elevated temperatures.

The above is only the preferred embodiment of the invention. Ordinary technicians in the technical field can make several improvements and refinishes without departing from the principle of the invention. These improvements and refinishes should also be considered as the protection scope of the invention.

What is claimed is:

1. A method for a thermal simulation of hydrocarbon-water-rock interactions based on isotope tracing comprising the steps:

step 1: conducting hydrocarbon-water-rock thermal simulation experiments: combining n-eicosane, water, and grains of a feldspar in a reactor, and sealing the reactor under argon; heating the reactor for a reaction and quenching the reactor with water to room temperature at an end of the reaction to produce a plurality of samples;

step 2: testing the plurality of samples obtained in step 1 after the reaction to obtain data comprising a composition and a content of a gas product, an isotopic composition of the gas product, an isotopic composition of a water solution, an isotopic composition of an authigenic clay, high-field nuclear magnetic resonance (NMR) spectra of liquid hydrocarbons and the water solution in the plurality of samples, a mineral texture, and a mineral composition;

step 3: deciphering genesis of the hydrocarbon-water-rock interactions: based on the data obtained in step 2, analyzing genetic mechanisms of a mass exchange and an occurrence of the hydrocarbon-water-rock interactions;

wherein in step 1, the n-eicosane is $n-C_{20}H_{42}$ or $n-C_{20}D_{42}$; the water is $H_2^{18}O$, $D_2^{18}O$, or $D_2^{18}O$; and the feldspar is K-feldspar.

2. The method according to claim 1, wherein a mass ratio of the n-eicosane, the water, and the grains of the feldspar used in step 1 is (3-9):(2-7):(0.5-1).

3. The method according to claim 1, wherein the reactor used in step 1 undergoes a pretreatment and the pretreatment comprises heating the reactor at 740-760° C. for 7-9 hours, then cleaning the reactor with acetone and distilled water, and drying the reactor at 60° C.

4. The method according to claim 1, wherein a temperature used in step 1 to heat the reactor is 339-341° C., and a time for the reaction is 9-11 days.

5. The method according to claim 1, wherein a gas chromatography-mass spectrometry system is used to detect the composition and the content of the gas product of step 2.

6. The method according to claim 1, wherein a gas chromatography isotope ratio mass spectrometer is used to detect the isotopic composition of the gas product remaining after testing the composition and the content of the gas product in step 2.

7. The method according to claim 6, wherein detecting the isotopic composition of the water solution in step 2 comprises: separating liquid products in the reactor to obtain a first upper liquid hydrocarbon and a first lower water solution; evaporating the first lower water solution at 75-85° C. to obtain a remaining lower water solution, and purifying the remaining lower water solution using bromoethane filtration, activated carbon filtration, and $C_{18}$ molecular sieve in sequence; and using the gas chromatography isotope ratio mass spectrometer to test an isotopic composition of the remaining lower water solution.

8. The method according to claim 1, wherein testing the isotopic composition of the authigenic clay in step 2 comprises: separating liquid products in the reactor to obtain a first upper liquid hydrocarbon and a first lower water solution; centrifuging the first lower water solution and collecting a clay precipitate; separating the clay precipitate on a surface of the grains of the feldspar in the reactor, mixing the clay precipitate obtained from centrifugation and from the surface of the grains of the feldspar to obtain a clay precipitate mixture, washing the clay precipitate mixture with dichloromethane and water in turn, and then using a gas chromatography isotope ratio mass spectrometer to detect the isotopic composition of the authigenic clay.

9. The method according to claim 8, wherein testing the high-field NMR of the liquid hydrocarbons and the water solution in step 2 comprises: separating liquid products in the reactor to obtain a second upper liquid hydrocarbon and a second lower water solution; removing water from the second upper liquid hydrocarbon using anhydrous copper sulfate to obtain the liquid hydrocarbons; mixing the liquid hydrocarbons and the second lower water solution with a deuterium-free reagent, and then using a high-field NMR to obtain the high-field NMR spectra of the liquid hydrocarbons and the second lower water solution respectively.

10. The method according to claim 1, wherein detecting the mineral texture and the mineral composition in step 2 comprises: drying the grains of the feldspar after the reaction, spraying gold on the grains of the feldspar, and using a scanning electron microscope (SEM) and an energy dispersive spectroscopy (EDS) to detect the mineral texture and the mineral composition.

11. The method according to claim 7, wherein testing the isotopic composition of the authigenic clay in step 2 comprises: separating liquid products in the reactor to obtain a second upper liquid hydrocarbon and a second lower water solution; centrifuging the the second lower water solution and collecting a clay precipitate; separating the clay precipitate on a surface of the grains of the feldspar in the reactor, mixing the clay precipitate obtained from centrifugation and from the surface of the grains of the feldspar to obtain a clay precipitate mixture, washing the clay precipitate mixture with dichloromethane and water in turn, and then using the gas chromatography isotope ratio mass spectrometer to detect the isotopic composition of the authigenic clay.

12. The method according to claim 9, wherein detecting the mineral texture and the mineral composition in step 2 comprises: drying the grains of the feldspar after the reaction, spraying gold on the grains of the feldspar, and using a scanning electron microscope (SEM) and an energy dispersive spectroscopy (EDS) to detect the mineral texture and the mineral composition.

* * * * *